United States Patent [19]

Hain et al.

[11] Patent Number: 5,165,896

[45] Date of Patent: Nov. 24, 1992

[54] CLAMPING MECHANISM FOR A DENTAL TOOL

[75] Inventors: Johann Hain, Heppenheim-Kirschhausen; Werner Schwarz, Heppenheim, both of Fed. Rep. of Germany

[73] Assignee: Siemens Aktiengesellschaft, Munich, Fed. Rep. of Germany

[21] Appl. No.: 857,278

[22] Filed: Mar. 25, 1992

[30] Foreign Application Priority Data

Mar. 28, 1991 [EP] European Pat. Off. ........ 91105052.4

[51] Int. Cl.[5] .................................................. A61C 1/14
[52] U.S. Cl. ........................................ 433/129; 433/127
[58] Field of Search ........................ 433/127, 128, 129

[56] References Cited

U.S. PATENT DOCUMENTS

| | | | |
|---|---|---|---|
| 2,983,519 | 5/1961 | Staunt | 433/127 |
| 4,015,335 | 4/1977 | Nash et al. | 433/129 |
| 4,370,132 | 1/1983 | Wohlgemuth | 433/128 |
| 4,874,314 | 10/1989 | Fleer et al. | 433/129 |
| 5,040,980 | 8/1991 | Heil | 433/127 |

FOREIGN PATENT DOCUMENTS 0273259 12/1987 European Pat. Off. .
2509985 1/1983 France .

*Primary Examiner*—John J. Wilson
*Attorney, Agent, or Firm*—Hill, Van Santen, Steadman & Simpson

[57] ABSTRACT

A clamping arrangement for clamping a cylindrical shaft of a tool in a dental handpiece includes a clamping sleeve having resilient tongues for gripping the cylindrical shaft and being capable of being moved radially outward by an adjustable plunger to release the shaft. In order to achieve a largely wear-free tool guidance, the tool shaft is held at least at its distal end of the tool in a guide bushing, which is firmly joined to the hollow shaft. The guide contains an arrangement which enables axial mobility of the plunger, prevents twisting of the plunger so as to enable transmission of the force between the plunger and a manipulator which actuates the plunger.

14 Claims, 3 Drawing Sheets

CLAMPING MECHANISM FOR A DENTAL TOOL

BACKGROUND OF THE INVENTION

The present invention is directed to a clamping mechanism in a socket formed by a hollow clamping sleeve which will hold a tool shaft of a dental tool. The clamping sleeve adjacent an end facing away from the tool has longitudinally extending slots so that the portion of the sleeve forms resilient tongues for retaining the tool shaft in a clamped position. In addition, the sleeve can be moved to a releasing position by a manipulator or button being pressed to engage a plunger which has an outwardly tapering surface engaging internal tapered or conical surfaces of the fingers.

U.S. Pat. No. 4,874,314, whose disclosure is incorporated herein by reference thereto and which claims priority from German Patent Application 36 44 055, discloses a clamping arrangement to hold a dental tool in a dental handpiece. The arrangement includes a hollow sleeve having slots adjacent an end facing away from the tool to form resilient fingers or tongues, which will engage a cylindrical surface of the tool. Each of the fingers has inwardly tapering surfaces engageable by corresponding tapering surfaces of a plunger which can be axially moved to cause the fingers to disengage the shaft of the tool. In this clamping mechanism, the plunger can be actuated by a manipulator and also assumes the guidance of the tool shaft. Since the plunger should be freely movable in an axial direction as a result of its function, an imprecise guidance of the tool shaft having untrue running of the tool can occur, particularly given an imprecision in the manufacture and fit. Higher running noises, as well as increased wear on the parts, will result from these imprecise fits. Increased wear, in particular, can also be attributed to the fact that the plunger is not secured against torsion.

SUMMARY OF THE INVENTION

The object of the present invention is to provide an improved clamping device that guarantees a largely wear-free tool guidance with optimum true running and to eliminate the creation of noise as a result of this optimally true running.

To accomplish these goals, the present invention is directed to an improvement in a clamping mechanism for clamping, in particular, a dental tool having a cylindrical shaft, said clamping arrangement including a hollow shaft that can be placed in rotation for the acceptance of a clamping sleeve that holds the tool shaft and has longitudinal slots on an end facing away from the tool to form resilient tongues for retaining the tool shaft in the clamped position, the tongues, for the purpose of removing a tool, are capable of being brought radially outward into a retracted position with an axially adjustable plunger actuated by a manipulator, an end of the plunger comprises an outer cone at its ends facing the clamping sleeve, and the clamping sleeve includes an internal cone corresponding therewith so that when the plunger is guided freely movable in the hollow shaft in an axial direction but the clamping sleeve is held axially immobile in the hollow shaft. The improvements are that the tool shaft is held at least at a distal end of the shaft in a guide firmly joined to the hollow shaft and the guide, in turn, contains means which guarantees the axial mobility of the plunger and prevents twistability and also enables transmission of forces between the plunger and the manipulator upon actuation of the manipulator.

In that the tool shaft is preferably guided at two locations placed relatively far apart and the shaft guidances are rigidly joined to the hollow shaft, the abovementioned disadvantages that were attached to previous embodiments are avoided. The guidance is advantageously executed as a bushing and can be both an integral component part of the hollow shaft, as well as a separate component part firmly joined to the hollow shaft.

The means of the guide are recesses for the passage of power transmission parts interacting with the manipulator. These recesses can be arranged both on an outside circumference, as well as an inside circumference of the guide. The guide proximate to the tool is advantageously a bushing that is a component part distinct from the clamping sleeve, because one then enjoys freedom with respect to the selection of material for the guide bushing and this can be advantageously manufactured of a material selected from a group consisting of hardened steel and hard metal. These materials cannot be employed for the clamping sleeve. As already mentioned, the guide located at a distal end from the tool can, advantageously, be an integral component part of the hollow shaft in that the hollow shaft and guide are fashioned as one piece. When, in conformity with other advantageous developments, the guide at the distal end from the tool contains a detente or shoulder which will limit the insertion depth of the tool shaft, it is assured that an easy running and mobility of the plunger remains preserved, given vibrations.

Other advantages and features of the invention will be readily apparent from the following description of the preferred embodiments, the drawings and claims.

DESCRIPTION OF THE PREFERRED EMBODIMENTS

The principles of the present invention are particularly useful when incorporated in a clamping arrangement for holding a dental tool, such as 5, and a head housing 1 of a dental turbine handpiece.

Figure 1:
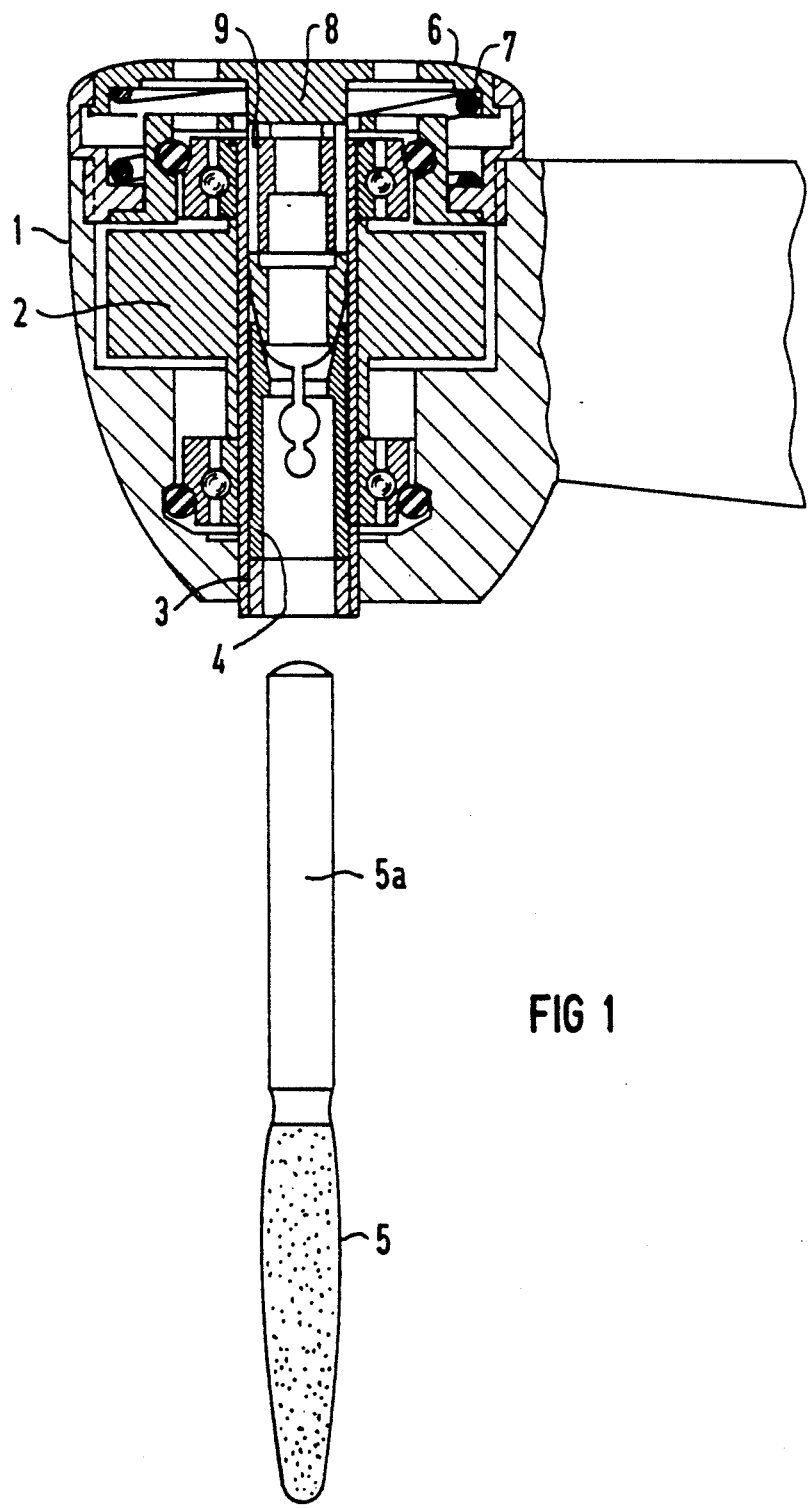
FIG. 1 is a cross sectional view with portions in elevation for purposes of illustration of a head housing of a dental turbine handpiece having a clamping mechanism according to the present invention together with a drill tool shown in a partially removed condition.
Figure 2:
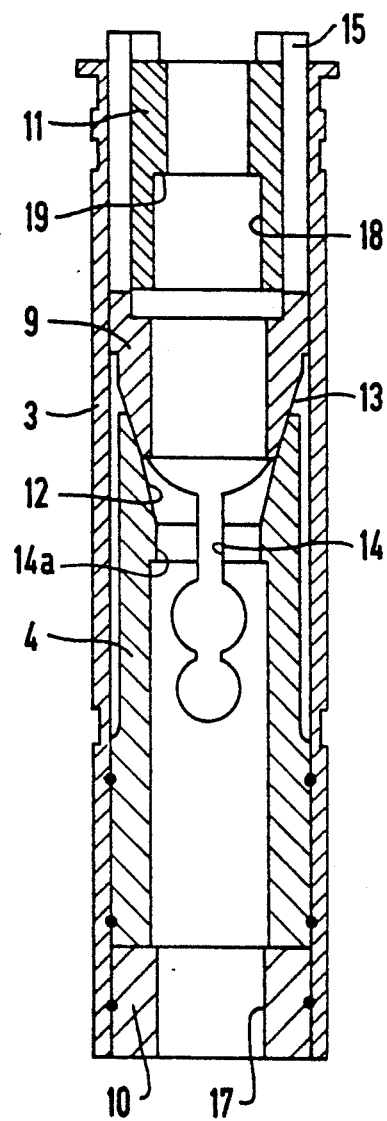
FIG. 2 is a cross sectional view of a clamping mechanism within the inserted tool taken along the lines II—II of FIG. 3.

The head housing 1 of a dental handpiece is illustrated as having bearings supporting a turbine rotor 2 in a conventional manner. The turbine rotor 2 drives a sleeve-shaped hollow shaft 3 in which a clamping sleeve 4 is mounted. The clamping sleeve 4 interchangeably holds, by a torsional holding, a cylindrical shaft 5a of a tool 5, which may be a drill, a miller or the like. The holding occurs by a simple axial insertion into the clamping device. Before removing the tool, a pressure cover or button 6, which is arranged at an end of the head housing 1 facing away from the tool, is pushed axially inward so that a pressure piston 8 will press against a spring force of a spring 7 onto a plunger 9, which is received for axial displacement in the hollow shaft 3 and which will then engage an end of the clamping sleeve 4 to cause a release of the tool. As illustrated in FIG. 2, the sleeve 4 has axially extending slots, such as 14, to form fingers or tongues with the tongues having internal tapered surfaces forming an internal cone 12. The plunger 5 has an external conical surface or cone 13, which engages the surface 12 to urge the fingers radially outward to release the shaft 5a of the tool. It should be pointed out that this portion of the clamping arrangement is substantially the same as that in the above-mentioned U.S. Patent, and reference is made thereto for a further description thereof.

A lower tool-proximate guide bushing 10 is secured in the lower end of the sleeve 3, as well as the clamping sleeve 4, which is also secured in the sleeve. At an upper or opposite end, a guide sleeve 11 is secured in the hollow sleeve 3. This securing can be, for example, by spot laser welding. The structure of the clamping sleeve 4, as mentioned above, is substantially the same as that described in greater detail in the above-mentioned U.S. Patent. It should be noted that, when the inward conical surface 12 is not engaged by the outside cone 13 of the plunger 9 and the tool is inserted, the tool shaft is reliably held in a clamping position by the resilient tongues of the cone 12 that form contact surfaces 14'. These contact surfaces 14' will release the tool shaft for removal of the tool when the cone 13 is moved axially to bias the internal cone 12 and the fingers radially outward.

The plunger 9 is held axially movable in the shaft 3 so that it can move down from a retracted position upon actuation of the pressure cover 6. As a consequence of the conical connection of the plunger and the clamping sleeve, the clamping tongues are pressed radially outward, as a result whereof the retaining force of the contact surfaces 14a is cancelled. After releasing the pressure cover 6, it will return to its initial position due to the force of the compression spring 7. As a result of the force components acting from the resilient sleeve and the shape of the surfaces 13, the plunger will be axially pressed back upward to its initial position.

Figure 3:
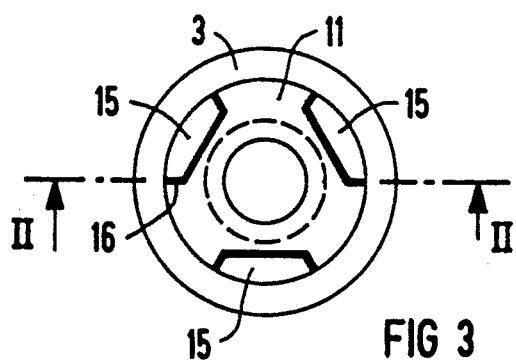
FIG. 3 is a top end view of the clamping mechanism of FIG. 2.

Referring to FIGS. 2 and 3, the plunger 9, at an end opposite the cone 13, has three webs or projections 15 which extend parallel to the axis of the tube 3. These webs or projections 15 are received in recesses or slots 16 formed in the distal end tool guide bushing 11 and have their upper end parts extending axially beyond the end surface of the guide 11 so as to be engageable with the pressure piston 8. Advantages in terms of fabrication can be achieved when, as shown, the webs 15 and the recesses 16 extend over an angular range of approximately 60° and are arranged with a circumferential spacing of approximately 120° so that the center of each of the extensions or webs 15 is approximately 120° from the center of the adjacent web.

Both the tool-proximate guide bushing 10 as well as the distal end tool guide bushing 11 are fashioned for accepting the tool shaft 5a with an exact fit. Both guide bushings in the illustrated embodiment comprise closed generated surfaces 17 for the bushing 10 and 18 for the inside circumference of the bushing 11. So that easy running and axial mobility of the plunger is preserved given vibrations, the insertion depth of the tool shaft is limited by an internal shoulder or detente 19 in the guide 11.

Figure 4:
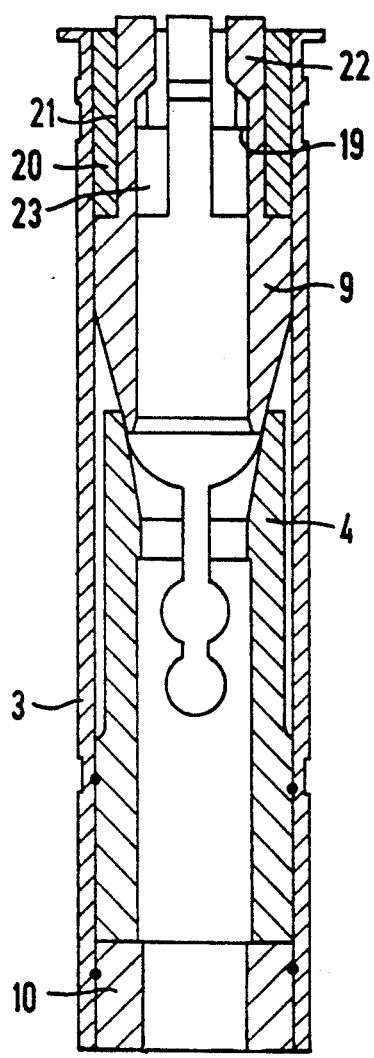
FIG. 4 is a cross sectional view of an embodiment of the clamping mechanism shown in FIG. 2, which cross sectional view is taken along the lines IV—IV of FIG. 5.
Figure 5:
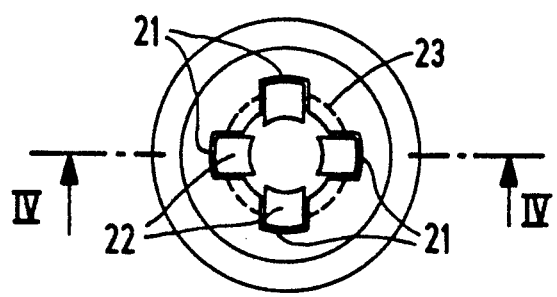
FIG. 5 is a top plan view of the clamping mechanism of FIG. 4.

An embodiment of the arrangement of FIGS. 2 and 3 is shown in FIGS. 4 and 5 and primarily involves the positioning of the recesses through which the power transmission elements or webs of the plungers interact with the pressure cover being arranged on an inner circumference of the guide bushing. As shown, the distal end tool guide bushing 20 is firmly joined to the hollow shaft 5 and has an internal circumferential surface provided with a plurality of recesses or slots 21, through which webs 22 of the plunger 9 are received. As in the above-described embodiment, a good guidance of the shaft end of the tool 5 is established by a generated surface 23 of the bushing, which, unlike the earlier embodiment, are interrupted by the slots 21.

As a result of the double shaft guidance, which are firmly connected to the hollow shaft, that simultaneously represents an anti-twist protection for the plunger, which is now only axially movable, an extraordinarily wear-free tool guidance having an optimally true running of the tool will occur. The clamping sleeve only has to absorb retaining forces for the tool shaft and no longer assumes any guide functions. The latter are assumed only by the guide bushings firmly joined to the hollow shaft. Because the lower or proximate tool guide bushing 10 is structurally distinct from the clamping sleeve 4, the former can preferably be formed of a hard metal, a material which cannot be used for the resilient element, such as the above-described clamping sleeve.

Although various minor modifications may be suggested by those versed in the art, it should be understood that we wish to embody within the scope of the patent granted hereon all such modifications as reasonably and properly come within the scope of our contribution to the art.

We claim:

1. In a clamping mechanism for clamping a dental tool having a cylindrical shaft, said mechanism including a hollow shaft receiving a clamping sleeve which holds a tool shaft, said clamping sleeve being longitudinally slotted at an end facing away from the tool to form resilient tongues for retaining the tool shaft in a clamped position, said tongues, for the purpose of removing the tool, being capable of being brought radially outward into a retracted position by an axially adjustable plunger actuated by an external manipulator, wherein the plunger includes an outside conical surface engaging an internal conical surface of the clamping sleeve, said plunger being guided freely movable in the hollow shaft in an axial direction while the clamping sleeve is being held axially immobile in the hollow shaft, the improvements comprising the hollow shaft at the distal end being provided with a tool guide firmly joined to the hollow shaft, the guide being formed with means for allowing axial mobility of the plunger while preventing twistability thereof and enabling the transmission of forces between the plunger and the external manipulator to enable actuation of said plunger.

2. In a clamping mechanism according to claim 1, wherein the guide is an integral component of the hollow shaft.

3. In a clamping arrangement according to claim 1, wherein the guide comprises a bushing firmly joined to the hollow shaft.

4. In a clamping mechanism according to claim 3, wherein the hollow shaft, at a proximal end adjacent the tool, is provided with a second guide bushing firmly joined to the hollow shaft and a separate component distinct from the clamping sleeve.

5. In a clamping mechanism according to claim 4, wherein each of the guide bushings is composed of a hard metal.

6. In a clamping mechanism according to claim 4, wherein each of the guide bushings is composed of hardened steel.

7. In a clamping mechanism according to claim 3, wherein the guide bushing is selected of a material chosen from a group consisting of hardened steel and hard metal.

8. In a clamping arrangement according to claim 1, wherein the means of the distal end tool guide bushing is a plurality of axially extending and circumferentially spaced slots, and said plunger has axial extensions being received in said slot and extending axially beyond the bushing for engagement with the manipulator.

9. In a clamping arrangement according to claim 8, wherein the slots are arranged on an outer circumference of the guide bushing and the guidance of the tool shaft is formed by a closed generated surface on an inner circumference of the bushing.

10. In a clamping arrangement according to claim 8, wherein the guide bushing includes an internal shoulder for limiting the depth of insertion of the tool shaft.

11. In a clamping arrangement according to claim 8, wherein the axial slots are arranged on the inside circumferential surface of the guide bushing and the guidance of the tool shaft is formed by a generated surface interrupted by said slots.

12. In a clamping mechanism according to claim 8, wherein the distal end tool guide bushing is integrated into the hollow shaft.

13. In a clamping arrangement according to claim 8, wherein the hollow shaft, at a proximal end relative to the tool, has a second guide bushing which is separate from the clamping sleeve.

14. In a clamping arrangement according to claim 13, wherein both the first-mentioned guide bushing and the second guide bushing are formed of a metal selected from a group consisting of hardened steel and hard metals.

* * * * *